United States Patent [19]

Frazier et al.

[11] Patent Number: 5,274,119
[45] Date of Patent: Dec. 28, 1993

[54] VICINAL DIOLS

[75] Inventors: Kevin A. Frazier; Margaret E. Schott, both of Midland, Mich.

[73] Assignee: The Dow Chemical Company, Midland, Mich.

[21] Appl. No.: 677,936

[22] Filed: Apr. 1, 1991

Related U.S. Application Data

[63] Continuation-in-part of Ser. No. 478,286, Feb. 9, 1990, abandoned, which is a continuation of Ser. No. 214,247, Jul. 1, 1988, abandoned.

[51] Int. Cl.$^5$ .................. C07D 403/08; C07D 403/12; C07D 403/02; C07D 207/452; C07C 103/32
[52] U.S. Cl. .................................. 548/521; 548/548; 548/546; 564/152; 564/153
[58] Field of Search .................. 548/548, 546, 521; 564/152, 153

[56] References Cited

U.S. PATENT DOCUMENTS

5,053,520  10/1991  Bieniarz et al. ............... 548/521

Primary Examiner—David B. Springer
Attorney, Agent, or Firm—Craig E. Mixan

[57] ABSTRACT

A group of functionalized linking agents are disclosed. The linking agents contain thiol reactive functionalities for the covalent reaction with sulfhydryl groups from the hinge-region of antibody fragments. The linking agents also contain masked aldehyde functionalities for covalent attachment of amine-containing therapeutic agents by Schiff base formation. Carrier systems capable of delivering compounds to targeted sites in vivo based on antigen-antibody interactions are constructed from these linking agents.

7 Claims, 2 Drawing Sheets

VICINAL DIOLS

RELATED U.S. APPLICATION DATA

Continuation-in-part of Ser. No. 478,286, Feb. 9, 1990, abandoned, which is a continuation of Ser. No. 214,247, filed Jul. 1, 1988, abandoned.

FIELD OF THE INVENTION

This invention relates to the general area of carrier systems capable of delivering compounds to targeted sites in vivo based upon antigen-antibody interactions. More specifically, this invention relates to the delivery of therapeutic agents to specific sites by linking the therapeutic agent to antibody fragments. This invention is particularly directed to univalent antibody fragments and synthetically recombined bivalent antibody fragments having a linking moiety containing a reactive or latent functionality suitable for attachment of the therapeutic agent of interest.

BACKGROUND OF THE INVENTION

Carrier molecules, such as whole antibody molecules or the F(ab')$_2$, Fab' or Fab fragments thereof, have been used in conjugation with a broad spectrum of pharmaceutical or cytotoxic agents, such as radioactive compounds, for the purpose of the targeted delivery of the therapeutic agents to tumor cells. The therapeutic agents are preferably covalently attached to the antibody protein in a fashion that leaves the antibody unchanged with respect to its ability to bind antigen, (see, for example, U.S. Pat. No. 4,671,958 and the references therein).

Among the common ways of performing this chemical attachment is the use of the carbohydrate groups which are present on whole antibody molecules (J. Immunological Methods, 99, 153 (1985)). This method involves the oxidation of the carbohydrate groups to aldehydes, followed by reductive amination using an amine and a reducing agent. Unfortunately, this approach is not applicable with most Fab' antibody fragments from which the carbohydrate-bearing Fc region has typically been enzymatically cleaved.

A similar method (U.S. Pat. No. 4,093,607) describes the periodate oxidation of a therapeutic agent that contains a glycol or hydroxy group, thus forming an aldehyde which is subsequently reacted with an antibody molecule or fragment. Attachment occurs via the formation of a Schiff base with the amino groups of the antibody. The Schiff base linkage is subsequently reduced.

Bifunctional cross-linking agents, including maleimide and bismaleimide compounds, have been used to attach Fab' fragments to other protein and non-protein species through free Fab' sulfhydryl groups, again with retention of antigen binding activity (see e.g. U.S. Pat. No. 4,659,839; Biochem. Biophys. Res. Commun., 99, 1146 (1981); and J. Biol. Chem., 257, 286 (1982)). Recently, bismaleimides have been used to prepare bispecific F(ab')$_2$ species containing thioether-linked Fab' fragments (J. Immunology, 139, 2367 (1987)). Heretofore, however, antibody fragments or synthetically recombined antibody fragments having a linking moiety containing an aldehyde or masked aldehyde functionality suitable for attachment of a therapeutic agent bearing a reactive amino functionality have been unknown.

SUMMARY OF THE INVENTION

The present invention is directed to a new class of multifunctional linking agents that bear one or more aldehyde or masked aldehyde functionalities. By masked aldehyde functionality is meant any protected aldehyde group or other functional group that can be converted to an aldehyde under conditions mild enough to avoid the denaturation of any associated proteins which may be present. Such groups include, but are not limited to, vicinal diols, acetals and hemiacetals and their thio analogs, cyanohydrins, hydrazones, imines, enamines, enol ethers and acetates. Vicinal diols are preferred functional groups for this purpose because of their controlled mild conversion to aldehydes by periodate oxidation. Most preferably, the diol unit itself is contained in a 5- or a 6-membered ring. In the 5-membered rings, the hydroxyls should be cis to configurationally allow for periodate oxidation.

The aldehyde functionality of the linking group is capable of binding with the free amino groups of therapeutic agents by Schiff base chemistry. The resulting covalent attachment of the therapeutic agent to the linking agent can be stabilized by subsequent reduction of the imine. As used herein, therapeutic agents refer to pharmaceutical or cytotoxic agents, such as, for example, radioactive compounds or complexes. To be useful for the present invention, the therapeutic agents must contain a free amino group or be capable of being modified to contain a free amino group that can react with the aldehyde portion of the linking agent to form a Schiff base (imine). Preferred therapeutic agents for the present invention are radioactive metal chelant complexes, for example, polyamine complexes or aminocarboxylate complexes.

The linking agents of the present invention also include thiol-reactive functionalities for covalent attachment to the free sulfhydryl groups generated by the mild reduction of whole antibodies or the fragments thereof via stable thioether bonds. As used herein, such thiol-reactive functionalities include maleimide and α-haloacetamide groups which readily react with the sulfhydryl groups of reduced antibody molecules or fragments. Maleimide groups are preferred.

More specifically, the present invention is directed to a compound of the formula (I):

wherein
R represents

X represents Cl, Br or I;

Z represents a straight-chained or branched alkylene group of 1 to 6 carbon atoms inclusive, a meta- or paraphenylene group or a $C_6H_3$ group;

m and n are independently 1 or 2;

T represents a divalent radical of 1 to 9 carbon atoms inclusive, optionally incorporating amide groups in the backbone; and Y represents a monovalent or divalent group containing at least one masked aldehyde functionality.

As used herein, the following terms have the following meanings; with respect to the definition of Z, $C_6H_3$ refers to a trivalent benzene ring; with respect to Y, a monovalent or divalent group which includes saturated or unsaturated acyclic or alicyclic radicals of 3 to 24 carbon atoms inclusive, or aromatic radicals of 6-24 carbon atoms, inclusive, all optionally incorporating amide groups in the backbone.

When n is 1, preferred compounds are of the formula (II):

wherein

T represents a divalent radical of 1 to 9 carbon atoms inclusive, optionally incorporating amide groups in the backbone; and represents a vicinal diol contained in a 5- or 6-membered aliphatic ring, provided that in a 5-membered ring the hydroxyl groups are cis to one another.

When n is 2, preferred compounds are of the formula (III):

wherein T and are as previously defined.

In the most preferred embodiments, T is wherein

W represents a straight-chained or branched alkylene group of 2 to 6 carbon atoms inclusive, or a phenyl group; and wherein the carbamoyl group is linked to

According to the present invention, the aforementioned linking compounds can be covalently bound to antibody fragments via stable thioether bonds with the sulfhydryl groups of mildly reduced antibody fragments. As used herein, antibody fragments refer to the antigen binding portion of the antibody molecule. The antibody fragments can be derived from the $F(ab')_2$ components of pepsin or of papain cleavage. Covalent attachment to the linking agent occurs from sulfhydryl groups located at the hinge region of the antibody fragment. The present invention is also directed to these antibody/linker conjugates of the formula (IV):

wherein R″ represents and m, n, Z and Y are as previously defined.

As used herein, Fab'-S- refers to an antigen-binding antibody fragment attached via a hinge region sulfhydryl group. In any of the cases in which m and n are not both equal to 1, the antibody fragments may be the same or different. For ease of preparation, the case where the antibody fragments are identical is often preferred.

According to the present invention, the aforementioned antibody/linker conjugates can be covalently attached to a free amino group of a therapeutic agent via the aldehyde functionality of the linking agent.

Therefore, the masked aldehyde functionality of the linking agent must first be converted to the aldehyde. Schiff base formation can occur with the free amino group of a wide variety of functionalities which include but are not limited to amines, hydrazines and semicarbazides. The resulting Schiff bases are often preferably reduced to stabilize the connection between the therapeutic agent and the antibody/linker conjugate. The present invention is also directed to a carrier system which comprises a therapeutic agent covalently bound to the antibody/linker conjugate previously described. Additional embodiments of the present invention are improved methods for the preparation of Fab' fragments from the mild reduction of F(ab')₂ fragments in which heavy-light chain disulfide bonds are simultaneously reduced. The first improved method comprises treating the material obtained from the reduction of F(ab')₂ fragments with 2,2'-dipyridyldisulfide at neutral pH to protect the hinge-region sulfhydryl group while reforming interchain disulfides and subsequently deprotecting the hinge-region sulfhydryl group by treatment with dithiothreitol at pH 4-5.

The second improved method comprises exposing the material obtained from the reduction of F(ab')₂ fragments to air until the heavy-light chain disulfide linkages are selectively reformed.

DETAILED DESCRIPTION OF THE INVENTION

The multifunctional linking agents of the present invention are characterized as containing one or more masked aldehyde functionalities in addition to one or more thiol-reactive functionalities suitably separated by spacer groups. By the term "suitably separated" is meant that the functionalities are sufficiently separated in space so that the subsequent attachment of the therapeutic agent or the antibody fragment is not prevented by steric hindrance. These linking agents are represented by the structure of formula (I):

wherein

R represents maleimido or α-haloacetamido;

Z represents a straight-chained or branched alkylene group of 1 to 6 carbon atoms inclusive, a meta- or para-phenylene group or a $C_6H_3$ group;

m and n are independently 1 or 2;

T represents a divalent radical of 1 to 9 carbon atoms inclusive, optionally incorporating amide groups in the backbone; and Y represents a monovalent or divalent group containing at least one masked aldehyde functionality.

Among the preferred embodiments are the following. For R, the preferred thiol-reactive group is maleimide which reacts specifically at pH 6-8 with a free sulfhydryl group of an antibody fragment. For Y, a group containing a masked aldehyde functionality is preferred over the aldehyde itself because the free aldehyde is prone to undesired reaction with other functionalities present in the antibody fragment, for example, with free amino groups. Therefore, it is preferable to generate the aldehyde from the masked aldehyde functionality after formation of the antibody/linker conjugate. Of the masked aldehyde functionalities, the vicinal diol group, which is easily converted to two aldehyde groups by the mild oxidation with periodate, is preferred. Cyclic vicinal diols in which both resulting aldehyde groups are retained within the linking agent are most preferred. It is further preferred that one of m or n is 1 while the other is 2, i.e., that the sum of m plus n is 3.

When n is 1, preferred compounds are of formula (II):

wherein

T represents a divalent radical of 1 to 9 carbon atoms inclusive, optionally incorporating amide groups in the backbone; and represents a vicinal diol contained in a 5- or 6-membered aliphatic ring, provided that in a 5-membered ring the hydroxyl groups are cis to one another.

When n is 2, preferred compounds are of the formula (III):

wherein T and are as previously defined.

In the most preferred embodiments, T is wherein

W is a spacer group, or a group capable of providing a spacer between the protein conjugation functionality and the masked aldehyde functionality. In one embodiment, "W" represents a polypeptide, with the situation of the number and type of amino acid residues necessary to achieve the stated function of "W" being within skill of an ordinary artisan. In a preferred embodiment "W" represents a straight-chained or branched alkylene group of 2 to 6 carbon atoms inclusive or a phenyl group; and wherein the carbamoyl group is linked to The linking agents of the present invention can be prepared using procedures known in the art. The compounds of formula (I) can be conveniently prepared by forming the amide bond in the final step as indicated in Scheme A.

In this scheme, R, Z, Y, m and n are as previously defined and L represents a leaving group conventional of such amide forming reactions. The leaving group, L, can be hydroxide, halide, or alkoxide, the corresponding starting material being an acid, acid halide or ester respectively. With an acid starting material, i.e., L is -OH, a dehydrating agent such as dicyclohexylcarbodiimide is often required. The preferred leaving groups are activated esters, such as, for example, the N-hydroxysuccinimidyl or nitro-substituted phenyl esters which readily react with amino groups to form amides.

The starting materials are mostly known compounds (see, for example, J. Prakt. Chem., 327, 789 (1985) and Helv. Chim. Acta, 58, 531 (1975)) or can be readily prepared from known compounds (see, for example, J. Immunological Methods, 24, 321 (1978) and Anal. Biochem., 155, 95 (1986)).

The N-maleoyl amino acids can be conveniently prepared by the reaction of amino acid esters with maleic anhydride and the subsequent cyclization of the maleamic acid to the maleimide followed by hydrolysis of the ester. The N-maleoyl amino acids can preferably be converted to their activated esters by conventional esterification procedures.

The N-($\alpha$-haloacetyl)amino acids can be conveniently prepared by the reaction of amino acids or carboxyl-protected amino acids with an $\alpha$-haloacetyl halide, wherein the halogen is preferably bromine, chlorine or iodine, or with an activated ester of an $\alpha$-haloacetic acid, such as an N-hydroxysuccinimidyl ester. The N-($\alpha$-haloacetyl)amino acids or their carboxyl-protected derivatives can be converted to their activated esters by conventional esterification procedures.

The $Y(TNH_2)_n$ starting materials, which contain 1 or 2 amino groups in addition to a masked aldehyde functionality, are similarly known or capable of being prepared by conventional procedures. Because of the presence of amino groups, which react with aldehydes, only masked aldehyde functionalities are suitable at this stage.

The masked aldehyde functionalities can generally be prepared from the appropriate precursors by conventional procedures. For example, the preferred vicinal diols of the present invention can be prepared from the corresponding alkene by hydroxylation (epoxidation followed by hydrolysis) with hydrogen peroxide and formic acid or by oxidation with osmium tetroxide or with alkaline potassium permanganate. For the most preferred vicinal diols contained in a 5- or 6-membered ring, the cis oxidation of a cyclopentene or cyclohexene substrate with osmium tetroxide or alkaline permanganate is preferred. For the subsequent periodate oxidation of the cyclopentanediol to be allowed, the adjacent hydroxyls must be in a cis relationship. The cis relationship is not required for conformationally mobile cyclohexanediols.

Acetals and hemiacetals and their thio analogs can be prepared from the corresponding aldehyde by treatment with alcohols or thiols. Similarly cyanohydrins, hydrazones, imines, enamines etc. can be prepared from the corresponding aldehyde by treatment with cyanide, hydrazines, amines etc.

In addition to the masked aldehyde functionality, the $Y(TNH_2)_n$ starting materials must contain at least one or two amino groups. Therefore, the appropriate precursors, in the absence of the amino groups, must contain a group or groups which can be readily modified to contain an amino group. By a group readily modified to contain an amino group is meant a group having a substituent which can be readily converted into an amino group or a group which can readily react with another group which already bears an amino functionality. For example, besides containing a masked aldehyde functionality or the appropriate precursor thereof, Y can also contain one or two carboxylic acid functionalities. These carboxylates, preferably in the form of esters, can react with an excess of diamine compound according to conventional procedures to form amides bearing the requisite amino groups in the N-alkyl portion of the amide. Suitable diamine compounds include, but are not limited to, α, ω-diamines of 2 to 6 carbon atoms inclusive and meta- and para-phenylene diamines.

Scheme B

Scheme B illustrates the general synthetic approach to one category of preferred linking agents. For example, a mono- or dicarboalkoxy substituted cyclopentene or cyclohexene can be oxidized to the corresponding cis-1,2-diol with osmium tetroxide. Treatment of the carboalkoxy substituents with an excess of the appropriate diamine provides the corresponding N-(aminoalkyl)carbamoyl compound. Finally, the N-(aminoalkyl)carbamoyl compound can be reacted with an activated ester of a N-maleoyl amino acid to give the linking agents of the present invention. As used in Scheme B, the symbols n, W, Z and are the same as previously defined. The symbol represents a 5- or 6-membered cycloalkene and alk represents an alkyl group of 1 to 4 carbon atoms inclusive.

The linking agents of the present invention can be covalently bound to antibody fragments via stable thioether bonds which involve reaction of sulfhydryl groups from the hinge region of the antibody fragment with the maleimide or α-haloacetamide portion of the linking agents. The antibody fragments which can be used in the antibody/linker conjugates described herein can be prepared by techniques well known in the art. It is well known, for example, that F(ab')$_2$ antibody species can be split into identical Fab' subunits by chemical reduction. The Fab' subunits can be reattached through a "natural" disulfide bridge to give back F(ab')$_2$ species which retain their ability to bind antigen (Science, 229, 81, Jul. 5, 1985).

The antibodies which are useful in the practice of the present invention include antibodies to any of the antigens which are known to be effective as in vivo tumor markers, such as, for example, TAG-72 (tumor associated glycoprotein -72).

Antibodies of the subclass I$_g$G$_1$ are preferred for use in the present invention. Highly specific monoclonal antibodies of this class can be produced by hybridization techniques well known in the art, see for example, Kohler and Milstein (Nature, 256, 495, (1975); and Eur. J. Immunol., 6, 511, (1976)). Such antibodies normally have a highly specific reactivity. In the antibody targeted therapeutic systems of the present invention, antibody fragments directed against any desired antigen or hapten may be used. Preferably the antibody fragments are derived from monoclonal antibodies having high specificity for a desired epitope(s). Antibody fragments used in the present invention may be directed against, for example, tumors, bacteria, fungi, viruses, parasites, mycoplasma, differentiation and other cell membrane antigens, pathogen surface antigens, toxins, enzymes, allergens, drugs and any biologically active molecules. The antibody/linker therapeutic systems are particularly preferred for the diagnosis and/or treatment of various cancers.

An antibody/linker therapeutic system which is directed against a particular cancer will localize onto tumor cells in vivo by virtue of the antigen-antibody fragment binding interaction. The therapeutic system can be used for diagnostic purposes, provided that the therapeutic agent attached to the multifunctional linker contains an imagible radioisotope and that the background in the region of the tumor is sufficiently low to allow images to be obtained. Also, the therapeutic system can be used for cancer treatment provided that the therapeutic agent contains a radioisotope which has suitable nuclear properties for the killing of cells. The utility of the therapeutic system can be evaluated in vivo using tumor-bearing nude mice as follows. A suitably buffered solution of the antibody fragment-multifunctional linker conjugate, bearing a chelated radioisotope as the preferred therapeutic agent, is injected into nude mice bearing xenographed human tumors. At appropriate time points the animals are sacrificed and the radioactivity in various tissues (tumor, blood, liver, kidney, spleen, etc.) is measured. A control experiment utilizing an irrelevant antibody can be conducted for comparison.

Figure 1:
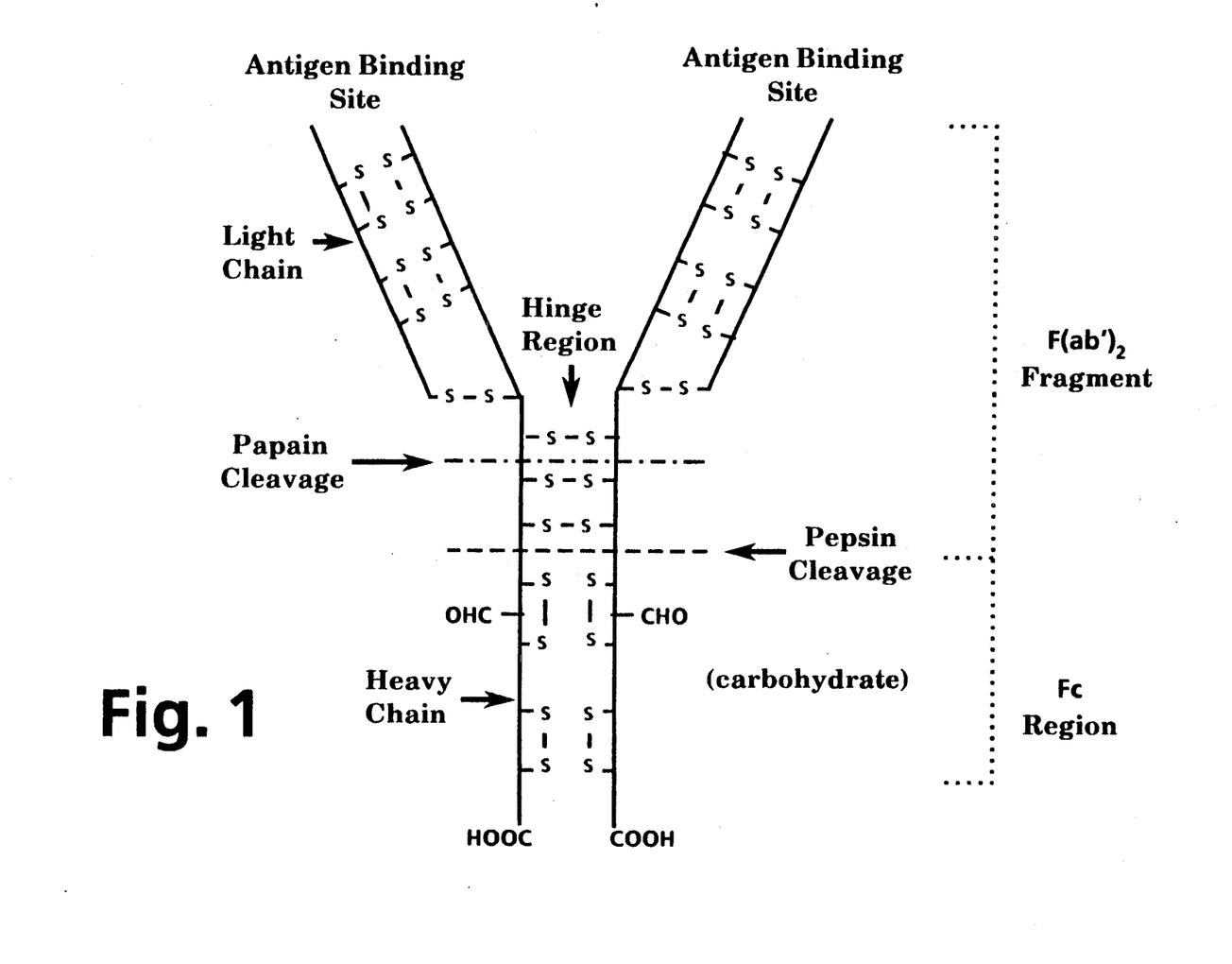
FIG. 1 is a schematic representation of an antibody molecule or immunoglobulin of the $I_gG$ class, more particularly of the murine $I_gG_1$ subclass.

An antibody molecule of the I$_g$G class, as depicted in FIG. 1, can be converted by enzymatic and chemical treatments into a Fab' fragment having at least one free sulfhydryl group in the hinge-region. The whole antibody can first be treated with an enzyme, either pepsin or preactivated thiol-free papain (J. Immunological Methods., 53, 133 (1982)), which effects a site-specific cleavage of the two heavy chains, removing the Fc portion of the antibody. The resulting F(ab')$_2$ fragment can be subjected to mild reduction which preferably cleaves the disulfide bonds joining the heavy chains without cleaving intrachain disulfide bonds. The two resulting Fab' fragments, each containing at least one free sulfhydryl group in the hinge region, can be coupled with the linking agents to produce the antibody/-linker conjugate. Since the hinge region is located distant from the antigen-binding site, the antigen-binding ability of the antibody fragment is unaffected.

Figure 2:
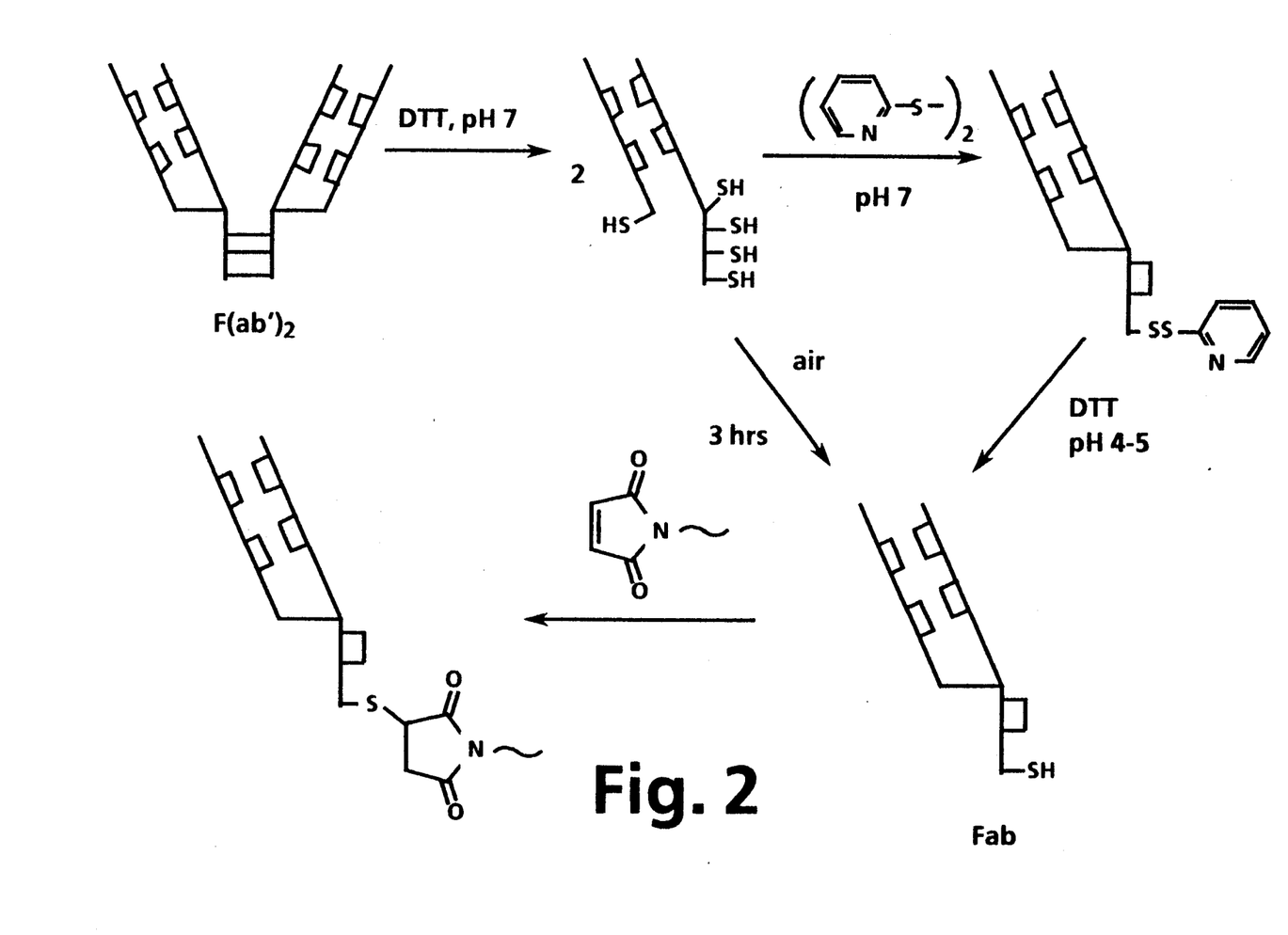
FIG. 2 depicts the general reaction scheme for preparing pepsin derived Fab' antibody fragments and their reaction with maleimides.

FIG. 2 illustrates the chemical aspects of this process. The F(ab')$_2$ fragments, obtained by the pepsin or papain cleavage of the whole antibody, can be subjected to mild reduction using dithiothreitol (DTT) at neutral pH. Although intrachain disulfide bonds are immune to reduction under these conditions, the disulfide bonds between the heavy and the light chains can be just as susceptible to reduction as the disulfide bonds between the heavy chains. The heavy-light chain disulfide bonds can be reformed by either of two selective processes. Treatment of the DTT reduced material with 2,2'-dipyridyl disulfide at neutral pH can modify the hinge-region sulfhydryl group with a 2-thiopyridyl group while, at the same time, can reform the heavy-light chain disulfide bonds. Pairs of appropriately spaced intra heavy chain sulfhydryl groups, derived from multiple interchain disulfides, can be similarly oxidized to disulfides. The "protected" hinge-region sulfhydryl group can be selectively deprotected by treatment with DTT at pH 4–5. Alternatively and preferably, the Fab' with a free hinge-region sulfhydryl group can be provided by air oxidation of the DTT reduced F(ab')$_2$. Simply leaving the reduced fragments exposed to air at ambient temperature for an appropriate period of time, can result in the selective reformation of the heavy-light chain disulfide linkages prior to significant reformation of the heavy-heavy interchain bonds. The appropriate period of exposure can be readily ascertained by conventional monitoring procedures such as sodium dodecyl sulfate polyacrylamide gel electrophoresis (SDS-PAGE), run under non-reducing conditions. These two alternative methods for the reformation of the heavy-light chain disulfide bonds represent improvements over the known processes and are also the subject of the present invention.

For example, the 2,2'-dipyridyl disulfide reagent (PDS) is preferred over 5,5'-dithio-bis(2-nitrobenzoic acid) (DTNB) for the modification of reduced heavy-light chain pairs because the pyridyl sulfide protecting group can be removed under conditions which are more selective than those for the thionitrobenzoic acid group. In other words, the disulfide bond of the pyridyl protecting group can be reduced at a low pH of 4–5 due to the formation of the protonated pyridone species. At this relatively low pH, concomitant reduction of other disulfide bonds in the Fab' will be negligible.

The hinge-region sulfhydryl group of the Fab' serves as the site of attachment of the antibody fragments to the linking agent. The sulfhydryl group can add to the maleimido functionality at ambient temperature and neutral conditions in a Michael type addition. Similarly, the sulfhydryl group can displace the halo-substituent in the α-haloacetamido functionality in a nucleophilic substitution. In each case, stable thioether linkages are effected.

The antibody/linker conjugates of the present invention contain masked aldehyde functionalities designed for the covalent attachment of therapeutic agents which have free amino groups. To effect this attachment the masked aldehyde functionalities must first be converted to aldehydes. The acetals and hemiacetals and their thio analogs, along with cyanohydrins, hydrazones, imines, enamines etc., can be hydrolyzed to the corresponding aldehyde. Vicinal diols can be oxidized with periodate to a pair of aldehydes. Reaction of the aldehyde of the antibody/linker conjugate with the amine of the therapeutic agent, results in the formation of a Schiff base (imine). The resulting Schiff base is preferably reduced to an amine to stabilize the carrier system derived by combining the therapeutic agent to the antibody/linker conjugate.

Scheme C illustrates the chemistry by which the therapeutic agent (-agent) is combined with the antibody/linker conjugate for one of the preferred embodiments of masked aldehyde functionalities. The cyclic vicinal diol can be oxidized at pH 6.0 with sodium periodate to a dialdehyde. Sequential reaction of the amine-containing therapeutic agent with the aldehyde and subsequent reduction with sodium cyanoborohydride results in the incorporation of the therapeutic agent. This incorporation, represented by can be an association of one amine containing therapeutic agent with one of the aldehyde groups, of two amine containing therapeutic agents with the two aldehyde groups, or of one amine containing therapeutic agent with both of the aldehyde groups.

By virtue of the ability of the antibody fragment to deliver the bound therapeutic agent directly to the site of a tumor, the present invention also includes a method for the diagnosis or treatment of cancer in a mammal by administration of the carrier systems comprising an amine containing therapeutic agent covalently bound to the antibody/linker conjugates of the present invention.

The following examples are given to illustrate the invention, and should not be construed as a limitation thereof.

EXAMPLE 1: PREPARATION OF THE 2,3-DIHYDROXYPROPYLAMIDE OF N-MALEOYL-β-ALANINE (A)

The N-hydroxysuccinimidyl ester of N-maleoyl-β-alanine (0.266 g, 1 mmol) was dissolved in 15 mL of acetonitrile. 3-Amino-1,2-propanediol (0.91 g, 1 mmol) dissolved in 2 mL of methanol was then added dropwise at room temperature. Some initial solids formation was observed but this dissolved by the time addition was complete. After the diol had been added, thin layer chromatography, TLC (4/1 EtOAc/MeOH) indicated the reaction was complete. The solvents were removed under reduced pressure and purification of the crude material was attempted by silica gel column chromatography (EtOAc/MeOH mixtures).

The chromatography of the diol A is problematic and clean separation of product from N-hydroxy-succinimide (NHS) is often incomplete. In order to avoid such problems the crude diol was converted to the acetonide by stirring in excess 2,2-dimethoxypropane with a catalytic amount of p-toluenesulfonic acid (pTSA). When all the diol was converted to acetonide (as monitored by TLC, 4/1 EtOAc/MeOH), solid NAHCO3 was added to neutralize the pTSA. The solution was filtered and the solvent was removed under reduced pressure. The acetonide obtained in this manner is then easily separated from NHS by column chromatography (2/1 EtOAc/Hexane).

Proton NMR 300 MHz (CDCl3) 7.14 (br s, 1H), 6.79 (s, 2H), 4.20 (m, 1H), 4.12 (m, 1H), 3.82 (br t, 2H), 3.60–3.68 (m, 1H), 3.39–3.49 (m, 1H), 3.24–3.34 (m, 1H), 2.55–2.63 (br t, 2H), 1.40 (s, 3H), 1.30 (s, 3H). C-13 NMR (DMSO-d6) ppm: 170.20, 169.90, 134.04, 74.37, 66.70, 41.81, 34.68, 34.33, 26.77, 25.12.

Approximately 4 g of acetonide was dissolved in 50 mL of methanol and 0.5 mL of concentrated HCl was added and the mixture stirred at room temperature. After 1½ hours (hr) a TLC (4/1 EtOAc/MeOH) indicated that starting material still remained. More methanol (30 mL) and concentrated HCl (0.5 mL) were added and the stirring continued. After an additional ½ hr the acetonide had been consumed, as indicated by TLC. The reaction mixture was stripped under reduced pressure to 5 mL of volume then 100 mL of acetonitrile was added and the solvent removed again under reduced pressure to azeotrope any remaining water. A yellow solid was obtained which was recrystallized from EtOAc/MeOH. A white solid (2.48 g) was obtained.

Proton NMR 300 MHz (DMSO-d6) 7.47 (br s, 1H), 6.73 (s, 2H), 3.92 (br s, 2H, OH), 3.74–3.85 (br t, 2H), 3.64–3.72 (m, 1H), 3.43–3.49 (br d, 2H), 3.18–3.40 (m, 2H), 2.48–2.56 (br t, 2H). C-13 NMR (DMSO-d6) ppm: 170.12, 169.58, 133.47, 70.19, 63.15, 41.73, 33.84, 33.77.

EXAMPLE 2: PREPARATION OF THE BISMALEIMIDO LINKING AGENT B a) Dimethyl-cis,trans,cis-2,3-dihydroxycyclohexane-4,5-dicarboxylic acid:

To a mixture of N-methylmorpholine oxide (6.21 g, 53 mmol) and 2.5 percent OsO4 in t-butanol (0.5 mL, ~0.05 mmol OsO4) in acetone (25 mL) and water (10 mL) was added, all at once, dimethyl cis-1,2,3,6-tetrahydrophthalate (9.91 g, 50 mmol). This material had been prepared by esterification of cis-1,2,3,6-tetrahydrophthalic anhydride. The reaction mixture was stirred vigorously overnight under a steady flow of nitrogen. When TLC (9:1; EtOAc:MeOH) indicated the reaction was complete, solvent and N-methylmorpholine by-product were removed in vacuo. The product (11.09 g) was obtained as an orange-brown oil and was used without further purification. H[1]-NMR (CDCl3) 2.10 (m, 2H); 2.62 (br s, 1H, OH); 3.13 (m, 1H); 3.69 (s, 3H); and 3.88 (m, 1H). C[13]-NMR (CDCl3): 29.50, 38.78, 51.88, 68.16, and 173.70.

b) Amidation of dimethyl-cis,trans,cis-1,2-dihydroxycyclohexane-4,5-dicarboxylic acid with ethylene diamine:

The dihydroxy-diester (6.09 g, 26.45 mmol) was stirred with ethylene diamine (36 mL, 0.53 mol) in 5–10 mL of dry methanol under a steady flow of nitrogen until the reaction was complete as indicated by TLC (2:2:1; CHCl3:MeOH:conc NH4OH). The excess ethylene diamine was removed under reduced pressure. Methanol (4–5 mL) was added to the viscous oil obtained and this mixture was added slowly to vigorously stirred tetrahydrofuran, THF, (400 mL). A white powder (3.12 g) was obtained by filtering; a second batch of solid (2.57 g) was obtained when the THF was removed and the procedure repeated. The materials obtained are mixtures of isomers (2 major and 1 very minor) as a result of epimerization α to the carbonyls caused by the basic ethylene diamine; the compositions of the first and second batches of material vary in isomer ratios; the complicated NMR (H[1] and C[13]) spectra and TLC evidence support this conclusion. This mixture of isomers was used without further purification or separation.

c) Reaction of the bis-amidoamine with N-maleoyl-β-alanine hydroxysuccinimide ester:

The bis-amidoamine (82 mg, 0.28 mmol), as a mixture of isomers, was dissolved in moist DMF (2 mL). Acetic acid (12 mL, 0.227 mmol) was added and a white precipitate formed. The N-hydroxysuccinimidyl ester of β-alanine (121 mg, 0.454 mmol) was added all at once. After ~4 hr, TLC (1:1; MeOH:CHCl$_3$) indicated starting materials had been consumed. The reaction mixture was slowly added to THF (125 mL) which was stirred rapidly. A tan solid formed which was filtered, collected and dried under vacuum. This product (90 mg) was again a mixture of isomers, as supported by the complicated NMR (H$^1$ and C$^{13}$) spectra; the maleimide peak is, however, distinct in both (6.85 ppm in the proton spectrum and 137.16 ppm in the carbon spectrum).

EXAMPLE 3: MILD REDUCTION OF F(ab')$_2$ INTERCHAIN DISULFIDE BONDS

A sample of F(ab')$_2$ (0.2 mg; from the pepsin digestion of mouse IgG1 antibody to TAG-72 antigen) in 0.1M pH 7.0 sodium phosphate (0.09 mL) was treated with 0.2M dithiothreitol (DTT) solution (0.01 mL; in 0.1M pH 7.0 sodium phosphate) for 10 minutes (min) at room temperature to reduce interchain disulfide bonds. The extent of the reaction was checked by SDS-PAGE on a 10 percent polyacrylamide gel after first quenching an aliquot (0.01 mL) with an excess of 0.2M iodoacetamide solution (0.02 mL, prepared in water) at room temperature. The results of the gel analysis (run under non-reducing conditions) showed complete reduction of both heavy-heavy (H-H) and heavy-light (H-L) interchain disulfide bonds. An examination of various pH conditions (pH 6.0, 7.0, and 8.0) and DTT concentrations demonstrated that while the reaction was slowed at low pH and low DTT concentrations, under none of the conditions tested was the reduction process selective for hinge-region H-H disulfide bonds. This may be explained by the fact that F(ab')$_2$ derived from pepsin-digested mouse I$_g$G$_1$ is believed to contain 3 inter-heavy chain disulfide bonds. Examples from the literature which claim selective reduction of hinge-region disulfide bonds typically involve the reduction F(ab')$_2$ species which contain only one H-H disulfide bond. These species include (i) F(ab')$_2$ derived from papain digestion (U.S. Pat. No. 4,659,839) or (ii) rabbit F(ab')$_2$ (Biochemistry, 20, 4229 (1981)).

EXAMPLE 4: METHOD I PREPARATION OF FAB'-SH BY SELECTIVE CHEMICAL REFORMATION OF H-L DISULFIDE BONDS a) Selective reformation of heavy-light disulfide bonds F(ab')$_2$ (1.0 mg) was mildly reduced in the manner described in Example 4. The sample was passed over a Dupont GF-250 HPLC column using as the mobile phase 0.4M pH 7.0 sodium phosphate containing 1 mM ethylenediaminetetraacetic acid (EDTA). The presence of EDTA helped to slow the re-oxidation of free sulfhydryl groups back to disulfide bonds and thus permitted the collection of reduced heavy-light chain pairs as a single peak by HPLC. (The HPLC buffer conditions were non-denaturing, allowing the heavy-light chain pairs to remain associated by hydrophobic interactions). The major peak was collected (1.5 mL) and treated with 0.002M 2,2'-dipyridyl disulfide (PDS) solution (75 μL; in DMF; final PDS concentration 0.1 mM) for 10 min at room temperature. Aliquots (10 μL) were quenched with 0.2M iodoacetamide solution (30μL; in water) both before and after treatment with PDS and analyzed by SDS-PAGE on a 10 percent polyacrylamide gel under non-reducing conditions. The results showed that the reduced heavy-light chain pairs (observed as two distinct bands near 25 kD) were converted into a single new species (near 50 kD) corresponding to Fab'-py, where 'py' represents the pyridyl group covalently attached to at least one hinge-region sulfhydryl group. In addition to the reformation of the "native" heavy-light disulfide bond, a new intrachain disulfide bond may also be formed from two heavy chain free sulfhydryl groups. However, since there are three hinge-region sulfhydryl groups, at least one retains a pyridyl group. Under the conditions described above, hinge-region free sulfhydryl groups on different heavy-light chain pairs do not get converted into disulfide bonds, i.e., F(ab')$_2$ species are not regenerated.

b) Selective reduction of hinge-region pyridyl disulfide bonds

A sample of Fab'-py was prepared as described in (a) above. After treatment with the dipyridyl disulfide, the product was isolated by high performance liquid chromatography (HPLC) using a Dupont GF-250 column with a mobile phase consisting of pH 7.0 0.2M sodium phosphate with 1 mM ethylenediamine tetraacetic acid (EDTA), then concentrated on an Amicon Centricon-30 centrifugal ultrafiltration device (MW cut-off 30,000), washed with 50 mM, pH 4.5 sodium acetate (2.0 mL), and made to 0.5 mL with the same buffer. Aliquots (90 μL each) were treated with 10 mM DTT solution (10 μL; in pH 4.5 sodium acetate) for 30 min at room temperature. The product was analyzed by SDS-PAGE on a 10 percent polyacrylamide gel after quenching an aliquot (0.03 mL) with 0.4M iodoacetamide solution (0.01 mL; in 0.4M, pH 7.0 sodium phosphate). The product (Fab'-SH) appeared identical to the starting material (Fab'-py) on the gel by this analysis; both showed one major band corresponding to a molecular weight of approximately 50 kD. Subsequent manipulations (See Example 6) with the newly formed Fab'-SH gave further evidence for the presence of a free hinge-region sulfhydryl group.

EXAMPLE 5: METHOD II PREPARATION OF FAB'-SH BY AIR OXIDATION

F(ab')$_2$ (2 mg) was mildly reduced in the manner described in Example 4. After treatment with DTT for 15 min, the sample was loaded (in ten aliquots of 0.1 mL each) onto QS-2B columns (Quik-Sep Sephadex G-25 columns; Isolab, Inc., Akron, Ohio) which had been pre-equilibrated with 0.1M pH 8.0 sodium phosphate (10 mL) and dried by centrifugation on a Sorvall RT-6000B. The centrifuge was run for 10 min at 16° C. with a spin rate of 4.2 (3000 rpm). The loaded QS-2B columns were placed in cut-off polypropylene tubes which are used as holders during this step in order to collect the "eluent". After a 5 minute sample equilibration period at room temperature, the columns were fitted snugly into capless 1.5 mL polypropylene collection tubes, then placed into empty holder tubes and centrifuged for 10 min at the settings given above. After centrifugation, the sample tubes (each containing approximately 0.1 mL) were stored at room temperature to allow the reoxidation of heavy and light chain free sulfhydryl groups into disulfide bonds. After 3.0 hr, an aliquot (0.01 mL) was quenched with 0.2M iodoacetamide (0.03 mL; in 0.1M pH 7 sodium phosphate) and analyzed by SDS-PAGE on a 10 percent polyacrylamide gel under non-reducing conditions. The gel showed a single major band near 50 kD that represented the disulfide bonded heavy-light chain pair, or Fab'-SH, with little or no trace of the individual heavy and light chain bands. Only a trace of the dimeric form, F(ab')$_2$ was present; this product was formed by reoxidation of hinge-region heavy chain sulfhydryl groups on different heavy-light pairs.

The procedure involved (1) mild reduction of the labile H-H and H-L disulfide bonds in F(ab')$_2$, (2) removal of the reducing reagent using a column centrifugation method, and (3) selective reformation of H-L disulfide bonds by air oxidation, leaving at least one free sulfhydryl group at the hinge-region of Fab'-SH. The column procedure served both to remove the reducing reagent and to aerate the solutions so that H-L reoxidation could occur in a relatively short period of time without the need for oxygen bubbling or extensive dialysis.

As further characterization, Fab'-SH was labeled with a fluorescent reagent, maleimido-5-fluorescein (Molecular Probes, Inc. Eugene, Ore.) in order to confirm the presence of at least 1 free hinge-region sulfhydryl group. Thus, an aliquot of Fab'-SH (0.05 mL, left for only 2 hr at room temperature, but 3.0 hr is preferred) was treated with the maleimide reagent at 1 mM (2 μL; in dimethylformamide) for 30 min and analyzed by SDS-PAGE. When illuminated with UV light before staining, the gel showed one major fluorescent band near 50 kD, corresponding to the fluorescent adduct of Fab'-SH, with only faint fluorescent bands observed at the individual heavy and light chain positions.

In order to quantitate the number of free hinge-region sulfhydryl groups on Fab'-SH, F(ab')$_2$ (0.8 mg) was mildly reduced and then processed over QS-2B columns in the manner described above. The pooled samples were treated with 0.02M 5,5'-dithiobis(2-nitrobenzoic acid) (0.4 mL; in 0.1M pH 7 sodium phosphate), then washed free of the reagent on a Centricon-30 unit. A portion of the product, Fab'-TNB, was made to 0.99 mL with the pH 7 buffer and treated with 0.1M 2-mercaptoethanol (0.01 mL; in pH 7 buffer). The UV-visible spectrum was recorded both before and after treatment with the thiol reagent. The concentrations of the newly generated "TNB" group and the Fab'-SH were calculated according to the method described in Analytical Biochemistry, 94, 75, (1979). Thus, the extinction coefficient for TNB at 412 nm was 14,150 L/mol. The concentration of Fab'-SH was calculated using an estimated MW of 50,000 and the convention that at 280 nm 1.0 ODU=1.48 mg/ml. (W. J. Mandy and A. Nisonoff, J. Biol. Chem. 238, 206 (1963)). A correction factor of $[0.176 \times A_{412(TNB)}] = A_{280}(TNB)$ was applied in order to obtain $A_{280}$ for Fab'-SH. The results showed that 1.1 TNB groups were released for every Fab'-SH subunit present. This result is in agreement with the concept that reoxidation of a pair of hinge-region heavy chain sulfhydryl groups leads to formation of an intrachain disulfide bond, leaving one free sulfhydryl group available for further reaction.

EXAMPLE 6: CONJUGATION OF A FLUORESCENT AMINE-CONTAINING AGENT TO AN ANTIBODY/LINKER CONJUGATE a) Preparation of the antibody/linker conjugate F(ab')$_2$ (0.47 mg) was mildly reduced in the manner described in Example 4 and the reduced heavy-light chain pair was isolated by GF-250 HPLC using 0.4M pH 7.0 sodium phosphate with 1 mM EDTA as the mobile phase. The isolated fraction (1.4 mL) was treated with 0.002M 2,2'-dipyridyl disulfide solution (0.075 mL; in 1:4 DMF/0.4M HPLC buffer) for 10 min at room temperature, then concentrated on a Centricon-30 unit and washed twice with 50 mM pH 4.5 sodium acetate buffer. The sample was made to 0.190 mL with the same buffer and treated with 0.02M DTT solution (0.01 mL; in pH 4.5 buffer) for 5 min at room temperature. Next, 0.1M solution of the 2,3-dihydroxypropylamide of N-maleoyl-β-alanine (A) (0.01 mL; in DMF) was added and the pH of the solution was adjusted by the addition of 0.4M pH 7.0 buffer (0.2 mL). After 30 min at room temperature the product was isolated by GF-250 HPLC using 0.4M pH 6.0 sodium phosphate with 1 mM EDTA as the mobile phase. The product was shown to consist of a single major band on a polyacrylamide gel run under non-reducing conditions.

b) Conjugation of a fluorescent amine-containing agent to the antibody/linker conjugate

One third of the above fraction was concentrated and made to 0.30 mL in 0.1M pH 6.0 sodium phosphate, then treated with 0.01M sodium meta-periodate solution (0.033 mL; in pH 6.0 buffer) for 30 min at 4° C. in the dark in order to oxidize the vicinal diol groups to aldehydes. The sample was then diluted to 2 mL with pH 6.0 buffer, concentrated, washed twice, made to 0.3 mL, and divided into aliquots of 0.1 mL each. To each aliquot was added a solution of fluorescein thiosemicarbazide (FTC, Molecular Probes, Inc.; 0.01 mL; in DMF)

to give final FTC concentrations of 1 mM, 0.1 mM, or 0.001 mM. A sample of Fab'-diol which had not been treated with periodate was used as a control. Immediately after the FTC additions, the samples were placed onto an automatic injector for GF-250 HPLC analysis using fluorescence detection (Ex=488 nm; Em=515 nm). The mobile phase, consisting of 30 percent methanol in 0.2M pH 7.0 sodium phosphate, was selected in order to remove excess FTC from the column in a short period of time. Peak areas for the fluorescent conjugates of oxidized Fab'-diol (now called Fab'-CHO, for aldehyde) were plotted as a relative fluorescence versus time of reaction. The results indicated that increasing the concentration of FTC allowed more of the fluorescent tag to be incorporated onto Fab'-CHO, presumably via formation of the Schiff base conjugate. This particular fluorescent reagent forms Schiff base conjugates which are stable and do not require the use of a reducing agent such as sodium cyanoborohydride. Virtually no fluorescence was observed in the control sample.

EXAMPLE 7: CONJUGATION OF A FLUORESCENT AMINE-CONTAINING AGENT TO THE OXIDIZED DIOL MOIETY OF AN ANTIBODY/LINKER CONJUGATE the samples were pooled and passed over the GF-250 HPLC column in two injections in order to remove the minor contaminating species, disulfide-reformed F(ab')2 (HPLC mobile phase was 0.4M pH 7.0 sodium phosphate with 1 mM EDTA). The Fab'-SH fractions were treated with a 1 mM solution of the bismaleimide-diol B (several additions of 2 μl each were made every 15 minutes until the product appeared on analytical HPLC).

After overnight storage at $-20°$ C. the samples were concentrated and passed over the GF-250 HPLC column and the peak corresponding to the desired product was collected, concentrated on a Centricon-30 unit, and washed with 0.1M pH 7.0 sodium phosphate (2×1.0 mL). A control sample of F(ab')2 was treated similarly at this step and in subsequent steps. The two samples were made to 225 μL with pH 6.0 buffer and treated with 0.0.1M sodium meta-periodate (25 μL; in pH 6.0 buffer) for 30 minutes at 4° C. in the dark. The samples were concentrated and washed with pH 6.0 buffer (2×1.0 mL), then made to 190 μL each and treated with 10 mM fluorescein thiosemicarbazide (10 μL; in DMF) for 30 minutes at 4° C. in the dark. After concentration and washing with pH 6.0 buffer (2×1.0 mL) the samples were analyzed by SDS-PAGE on a 10 percent polyacrylamide gel run under non-reducing and reduc- F(ab')2 (0.7 mg) was mildly reduced in the manner described in Example 4 (protein concentration was 0.9 mg/ml) and processed over QS-2B columns without temperature control. After 2.0 h at room temperature ing conditions. A photograph of the unstained gel under

UV light showed a fluorescent band near 100 kD in the product lane, but little or no fluorescence in the F(ab')₂ lane under non-reducing conditions. Under reducing conditions, the product lane showed a fluorescent band near 50 kD, corresponding to the crosslinked heavy chains. After staining with coomassie blue, protein bands were observed for all samples.

EXAMPLE 8: CONJUGATION OF A RADIOACTIVE CHELATE COMPLEX TO THE OXIDIZED DIOL MOIETY OF AN ANTIBODY/LINKER CONJUGATE a) Preparation of radioactive rhodium 105 complex of 6-(4-aminophenyl)methyl-1,4,8,11-tetraazoundecane ($^{105}$Rh-BA-2,3,2-TET)

(i) 2-Carbomethoxy-3-(4-nitrophenyl)propanoic acid methyl ester (p-nitrobenzyl malonate dimethyl ester), 1

2-Carbomethoxy-3-(4-nitrophenyl)propenoic acid methyl ester was made from the Knovenagle condensation of dimethylmalonate and p-nitrobenzaldehyde according to the method of J. Chem. Soc., 2125 (1927): Melting point observed (mp$_{obs}$)=133–134° C. Melting point reported in the literature (mp$_{lit}$)=136–137° C. 2-Carbomethoxy-3-(4-nitrophenyl)propenoic acid methyl ester (23.0 grams (g), 86.7 millimoles (mmole)) was dissolved in 175 milliliters (mL) of methanol (MEOH) under nitrogen and sodium cyanoborohydride (6.0 g, 95.5 mmole) was cautiously added to the stirred solution with cooling. The pH was adjusted to 4.0 with concentrated hydrochloric acid and the solution was stirred at 25° C. overnight. During the first 8 hrs the pH was readjusted from 6 to 4 on several occasions. The yellow methanol solution was poured into 700 mL of water and extracted with 3×200 mL portions of methylene chloride. The combined organic fractions were washed with 400 mL of saturated sodium bicarbonate and 400 mL of water, dried over magnesium sulfate and evaporated to a pale yellow oil on a rotary evaporator. The oil crystallized (mp=82–83° C.) upon standing and gave 2-carbomethoxy-3-(4-nitrophenyl)propanoic acid methyl ester (p-nitrobenzyl malonate dimethyl ester) in 93 percent yield (21.3 g, 81 mmole).

(ii) 3-(4-Aminophenyl)-2-carbomethoxypropanoic acid methyl ester (p-aminobenzylmalonate dimethyl ester), 2

The compound 2-carbomethoxy-3-(4-nitrophenyl)-propanoic acid methyl ester (p-nitrobenzylmalonate dimethyl ester) (2.00 g, 7.55 mmole) was dissolved in 70 mL of ethyl acetate containing 5 percent palladium on carbon (1.0 g; Aldrich Chemical Company) catalyst and was hydrogenated in a Parr shaker employing 50 psig of hydrogen at 22° C. Hydrogen uptake was rapid (15 minutes) and the mixture was maintained under hydrogen pressure for another 3 hrs. The pressure vessel was vented and flushed with nitrogen (N₂). The suspension was filtered through a pad of celite and the solvent was removed in vacuo using a rotary evaporator to provide 3-(4-aminophenyl)-2-carbomethoxypropanoic acid methyl ester (p-aminobenzylmalonate dimethyl ester) (1.76 g, 7.41 mmole) as a light yellow oil in 98 percent yield. The structure was confirmed by ¹H nuclear magnetic resonance (PMR) and ¹³C nuclear magnetic resonance (CMR) as well as mass spectroscopy (MS) spectral analysis.

(iii) 6-(4-(Aminophenyl)methyl)-1,4,8,11-tetraaza-5,7-dioxoundecane, 3

The compound 3-(4-aminophenyl)-2-carbomethoxy-propanoic acid methyl ester (p-aminobenzylmalonate dimethyl ester) (30.0 g, 0.126 mole) was added dropwise to a solution of ethylene diamine (75 g, 1.25 mole) in 150 mL of methanol under a nitrogen atmosphere with vigorous stirring (25° C). The solution was allowed to stir for 4 days until reaction was judged complete by thin layer chromatography (TLC). At this point the solvent and excess amine were removed in vacuo and the tan residue was dried overnight (70° C/0.1 mm) affording 36.3 9 of the desired compound 6-(4-(aminophenyl)-methyl)-1,4,8,11-tetraaza-5,7-dioxoundecane as a tan solid in 98 percent yield. An analytical sample was prepared by recrystallization from chloroform/hexane, mp=157–159° C., as a white crystalline powder. Structure was confirmed by PMR, CMR, and MS.

| Analysis | | | |
|---|---|---|---|
| | C | H | N |
| Calculated for C₁₄H₂₃O₂N₅: | 57.3 | 7.90 | 23.87 |
| Found: | 57.16 | 7.48 | 23.65 |

(iv) 6-(4-(Aminophenyl)methyl)-1,4,8,11-tetraazoundecane, (BA-2,3,2-Tet), 4

4 BA-2,3,2-tet

The compound 6-(4-(aminophenyl)methyl)-1,4,8,11-tetraaza-5,7-dioxoundecane (7.0 g, 23.9 mmole) was placed in a 3-necked, 250 mL round bottomed flask equipped with a stirrer and reflux condenser under a nitrogen atmosphere. Borane/tetrahydrofuran (THF) complex (150 mL, 150 mmole) (Aldrich Chem. Co.) was slowly added via a cannula under positive nitrogen pressure to the solid with stirring. A brief exotherm was noted and after it subsided, the stirred solution was taken to reflux for 48 hrs. The clear solution was stripped of solvent in vacuo leaving a glassy, semi-solid material. Methanol (100 mL) was cautiously added and hydrogen evolution was noted. The resulting solution was taken to dryness in vacuo. At this point, 100 mL of methanol was added and the solution saturated with anhydrous hydrogen chloride. The solution was brought to reflux under nitrogen for 1 h and stripped of solvent using a rotary evaporator. This cycle was repeated and the resulting crude hydrochloride salt of the desired compound was dissolved in 15 mL of water. This fraction was extracted with 2×20 mL portions of chloroform ($CHCl_3$) and the aqueous phase was then made basic (pH > 12) by the addition of 50 percent aqueous sodium hydroxide with cooling under argon. The basic solution was extracted with 6×75 mL portions of chloroform. These fractions were combined (no drying) and the chloroform was removed in vacuo to afford 5.8 g of crude amine as a yellow oil (91 percent). The crude material was purified by flash chromatography using a 16:4:1 solvent of chloroform:methanol:concentrated ammonium hydroxide and silica gel (Aldrich Chemical Co./Merck grade 60 230-400 mesh), ($R_f$=0.33 solvent 1). The structure of the purified product was confirmed by PMR, CMR, and MS.

| Analysis | | | |
|---|---|---|---|
| | C | H | N |
| Calculated for $C_{14}H_{27}N_5 \cdot 5HCl$: | 37.50 | 7.20 | 15.64 |
| Found: | 37.5 | 6.42 | 15.83 |

(v) $^{105}Rh$ was obtained using a system in which five flasks were interconnected via ground glass fittings in the following order; a first flask (a catch flask employed as a gas trap), a second flask (the reaction vessel), a third flask (trap #1), a fourth flask (trap #2), and a fifth flask (trap #3).

Into the reaction vessel was placed 10 mL of 2M NaOH. To trap #1 was added 150 mL of $CCl_4$, to trap #2 was added 150 mL of 2M NaOH and to trap #3 was added 150 mL of 2M NaOH. A quantity of Ruthenium metal (5.18 mg) which had been irradiated for 30 minutes in the 1st row p-tube at MURR (University of Missouri Research Reactor) on the previous day, was added to the reaction vessel. Stoppers were placed in the tops of the first four flasks. $Cl_2$ was bubbled through the apparatus for approximately 10 minutes, the solution in the reaction vessel turned bright yellow. A stream of air was then passed through the apparatus for 20 minutes and the reaction vessel was heated to reflux for approximately 5 minutes employing a heating mantle. During this process, the solution in the reaction vessel became clear and the $CCl_4$ in trap #1 turned bright yellow. The solution was removed from the reaction vessel and filtered through a 0.2 mm filter. A quantity of the reaction vessel solution (1.0 mL) was taken and diluted to 10 mL in a scintillation vial for counting. A quantity of 10 mL of each of the solutions contained in traps #1, #2 and #3 were also taken for counting. The solution in the reaction vessel contained the $^{105}Rh$.

(vi) The following example illustrates the preparation of rhodium chelate complexes using methods similar to those reported in Inorg. Chem., 1, 925 (1962).

Rhodium trichloride hydrate and lithium hydroxide (LiOH) (99.3 percent, anhydrous, −4+14 mesh) were obtained from Johnson Matthey and Alfa respectively.

Pharmacia Sephadex-SP ™ C-25 cation-exchange resin was purchased from Aldrich. Glass columns for chromatography were approximately 2.5×70 cm and fitted with a 29/42 ground glass joint at the top and a course glass frit and teflon stopcock at the bottom. The cation-exchange resin was prepared by adding 40 g of dry gel to 300 mL of 0.3N aqueous HCl with gentle stirring to form a slurry. The slurry was then transferred to a large graduated cylinder and allowed to swell over a 1.5 hr period. At several intervals during this period a portion of the 0.3N HCl was decanted off (in an effort to remove fines), additional 0.3N HCl was added, and the slurry was gently mixed. The column was poured by attaching a 1 liter Kugelrohr flask to the top of the column and transferring the slurry all at once. The gel was converted to the H+ form and packed by running 2-3 liters of 0.3N HCl through the column.

Samples (0.1 to 1.0 g) were chromatographed by dissolution in 5-10 mL distilled water and application of the solution directly to the top of the column. The solution was washed into the gel with several small portions of 0.3N HCl and eluted down the column with the same solvent. The solvent flow rate through the column was maintained with a Gilson Miniplus 2 peristaltic pump (3-4 mL per minute ($min^{-1}$)) and eluted sample peaks were detected at 254 nanometers (nm) with an Isco model UA-5 absorbance monitor with a model 1132 multiplexer-expander and type 6 optical unit. Neutral, negatively charged, and monopositively charged species eluted off the column quickly (0.5-1.5 hrs), di-positively charged species eluted off after 5-8 hrs, and more highly positively charged species remained at the top of the column.

With minor modifications, the method (Inorg. Chem., 17, 2822 (1978)) for the preparation of dichloro ($\beta$, $\beta'$, $\beta''$-triaminotriethylamine)rhodium(III) chloride was used. $RhCl_3 \cdot 3H_2O$ (0.308 g, 263.309 g $mol^{-1}$, 1.17 mmole) was added to a solution of BA-2,3,2-tet·5HCl (0.524 g, 447.71 g $mol^{-1}$, 1.17 mmole) in 30 mL of 0.1N LiOH. The red solution was refluxed for 5 minutes and then slowly titrated up to pH=6 over a 45 minute period using 0.1N LiOH (a total of 64.1 mL was used or 5.5 equivalents). The pH was monitored using color-pHast ™ indicator strips (obtained from Macalaster Bicknell Co.). After a total of approximately 1 hr of reflux the yellow-brown mixture was cooled, filtered, and the solvent removed on a rotary evaporator. The solid was dissolved in 10 mL of distilled water, filtered through a Celite TM pad on a fine porosity glass fritted filter and Gelman Acrodisc TM CR disposable syringe tip filter (obtained from Fisher Scientific), and applied to the top of a Sephadex-SP TM C-25 column. The di-positively charged species were eluted off the column as a single band with 0.3N HCl and a fraction was collected. The solvent was removed on a rotary evaporator and the yellow solid was dried at 300° C. in a vacuum oven yielding 0.205 mg of product (34.3 percent). The material was characterized by $^1$H and $^{13}$C NMR and fast atom bombardment mass spectroscopy. NMR spectroscopy indicated that the product existed in three isomeric forms.

| | Analysis | | |
|---|---|---|---|
| | C | H | N |
| Calculated $C_{14}H_{27}N_5Cl_3Rh·HCl·2H_2O$: | 30.73 | 5.90 | 12.80 |
| Found: | 30.5 | 5.4 | 12.5 |

(vii) Preparation of $[^{105}Rh(BA\text{-}2,3,2\text{-tet})Cl_2]^+$ $^{105}$Rhodium chloride (approximately 5 mCi/mL in 0.1N HCl) were obtained from the University of Missouri research reactor. Three milliliters of this stock solution were neutralized by the addition of 0.4 mL of 1.0M $NAHCO_3$. BA-2,3,2-tet (0.2 mL of a 10 mg/ml solution) was added with mixing. This solution was heated to 90° C. in a water bath for 1 h. Purification of the $^{105}$Rh complexes from any unbound metal and chelant was achieved by passing the solution through a Hamilton PRP-1 Chrompak Unit. The $^{105}$Rh complexes were eluted with a 30 percent acetonitrile/water wash. Analysis of this material indicated the presence of equal parts of the $[^{105}Rh(BA\text{-}2,3,2\text{-tet})Cl_2]^+$ and $[^{105}Rh(BA\text{-}2,3,2\text{-tet})\text{-}(Cl)(H_2O)]^{2+}$ complexes. The aquochloro complex was converted to the dichloro complex by making the solution 0.5N in HCl and heating to 90° C. in a water bath for an additional 30 minutes. The $[^{105}Rh(BA\text{-}2,3,2\text{-tet})Cl_2]^+$ complex was isolated and concentrated with the Hamilton PRP-1 Chrompak. The complex was characterized by comparison to known standard material using cation exchange chromatography and thin layer chromatography. Yields of greater than 85 percent with respect to the $^{105}$Rh were obtained.

b) Conjugation of a radioisotope-chelate complex

F(ab')₂ (1.0 mg) was mildly reduced in the manner described in Example 4 and processed over QS-2B columns (using a slightly modified procedure). After 2.5 hrs at room temperature an analytical HPLC profile of the pooled samples showed that a significant amount of disulfide-reformed F(ab')₂ was present (approximately 30 percent) in addition to Fab'-SH. The sample was treated with 10 mM EDTA solution (50 μL; in 0.1M pH 7.0 sodium phosphate) to prevent further disulfide bond formation. A solution of 1 mM bismaleimide-diol B solution was added in several portions (five additions of 5 μL every 10 minutes; in DMF), followed by several additions of 10 mM bismaleimide-diol solution (four additions of 1 μL). The reaction mixture was passed over the GF-250 HPLC column and the fraction corresponding to the antibody/linker conjugate was collected (mobile phase was 0.2M pH 6.0 sodium phosphate with 1 mM EDTA) and divided into two parts. The samples were treated with either 0.1M sodium metaperiodate (10 mM final concentration; stock solution was prepared in pH 6.0 buffer) or pH 6.0 buffer (as a control) for approximately 1 h at 4° C. in the dark, then concentrated on Centricon-30 units and washed (2×1.0 mL) with 0.1M pH 5.2 sodium acetate. Each sample (now approximately 50 μL) was treated with a solution containing ¹⁰⁵-Rh-BA-2,3,2-TET solution* (50 μL) and 0.01M sodium cyanoborohydride solution (10 μL; in pH 5.2 buffer) for 3 hrs at room temperature. The reaction mixtures were processed over QS-2B columns in order to remove excess reagents. The samples were analyzed by SDS-PAGE on a 10 percent polyacrylamide gel under non-reducing and reducing conditions, then stained with coomassie blue, destained, dried, and exposed to film. Under non-reducing conditions, both the protein staining and the autoradiography showed a major band near 100 kD corresponding to the desired product and a new band near 50 kD which appeared to be a "breakdown" product from the oxidation process. The F(ab')₂ control showed one major band by protein staining but only a faint band by autoradiography. Under reducing conditions, the product showed bands by autoradiography near 50 kD (heavy-heavy chain cross-linking) and 25 kD (heavy chains due to "breakdown" product), while the control showed only faint autoradiographic bands. The desired product can be further purified by GF-250 HPLC.

*The above solution containing ¹⁰⁵-Rh-BA-2,3,2-TET was prepared by mixing solutions A and B below in a 3:1 ratio: Solution A-¹⁰⁵-Rh-BA-2,3,2-TET at 1×10⁻⁸M in 30% acetonitrile/70% 0.1M pH 7.0 sodium phosphate, diluted 10-fold with pH 5.2 sodium acetate Solution B- "cold" Rh-BA-2,3,2-TET at 2×10⁻³M

What is claimed:

1. A compound of the formula wherein

R represents maleimido groups or α-haloacetamido groups;

Z represents a straight-chained or branched alkylene group of 1 to 6 carbon atoms inclusive, a meta- or para-phenylene group or a trivalent benzene group;

m and n are independently 1 or 2;

T represents a divalent radical of 1 to 9 carbon atoms inclusive, optionally incorporating amide groups in the backbone; and Y represents an alkane having a vicinal diol moiety.

2. A compound of claim 1 wherein the sum of m plus n is 3.

3. A compound of claim 2 having the formula wherein

W represents a straight-chained or branched alkylene group of 2 to 6 carbon atoms inclusive, or a phenyl group; and Y represents an alkane having a vicinal diol moiety.

4. A compound of claim 2 having the formula wherein

W represents a straight-chained or branched alkylene group of 2 to 6 carbon atoms inclusive, or a phenyl group, and Y represents a 5- or 6-membered alicyclic group having two hydroxyl groups on adjacent carbons, provided that when the alicyclic group is 5-membered the hydroxyl groups are cis to one another.

5. A compound of claim 3 wherein Y represents a 5- or 6-membered alicyclic group having two hydroxyl groups on adjacent carbons, provided that when the alicyclic group is 5-membered the hydroxyl groups are cis to one another.

6. The compound of claim 1 having the formula

7. The compound of claim 4 having the formula